(12) United States Patent
Tybinkowski et al.

(10) Patent No.: US 6,449,340 B1
(45) Date of Patent: Sep. 10, 2002

(54) ADJUSTABLE X-RAY COLLIMATOR

(75) Inventors: Andrew P. Tybinkowski, Boxford; Lidia Nemirovsky, Salem; Michael J. Duffy, Methuen; Jack M. Tybinkowski, Middleton, all of MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 09/764,798

(22) Filed: Jan. 18, 2001

Related U.S. Application Data

(60) Provisional application No. 60/221,944, filed on Jul. 31, 2000.

(51) Int. Cl.[7] .................................................. G21K 1/04
(52) U.S. Cl. ...................................... 378/150; 378/152
(58) Field of Search ................................ 378/150, 152, 378/4

(56) References Cited

U.S. PATENT DOCUMENTS

| | | | |
|---|---|---|---|
| 4,277,685 A | 7/1981 | Covic et al. ................ 250/445 |
| 4,361,902 A | * 11/1982 | Brandt et al. ................ 378/152 |
| 4,466,112 A | 8/1984 | Covic et al. .................... 378/7 |
| 4,920,552 A | 4/1990 | Hermens .................... 378/153 |
| 4,991,189 A | 2/1991 | Boomgaarden et al. ......... 378/4 |
| 5,299,250 A | 3/1994 | Styrnol et al. ................ 378/19 |
| 5,550,886 A | 8/1996 | Dobbs et al. .................. 378/19 |
| 5,563,924 A | 10/1996 | Winkelmann ................ 378/150 |
| 5,644,614 A | 7/1997 | Toth et al. ................... 378/147 |
| 5,669,017 A | * 9/1997 | Yamashina et al. ............ 396/6 |
| 5,674,361 A | * 10/1997 | Marinack ..................... 162/111 |
| 5,684,854 A | 11/1997 | Hughes ....................... 378/206 |
| 5,799,057 A | 8/1998 | Hoffman et al. ............ 378/147 |
| 6,085,893 A | * 7/2000 | Asai et al. ............. 198/377.08 |

FOREIGN PATENT DOCUMENTS

JP            401172740 A    *  7/1989    ................. 378/150

* cited by examiner

*Primary Examiner*—David P. Porta
*Assistant Examiner*—Elizabeth Gemmell
(74) *Attorney, Agent, or Firm*—McDermott, Will & Emery

(57) ABSTRACT

The present disclosure provides an adjustable collimator for collimating a beam of energy emitted from a focal spot of a beam source. The collimator is particularly intended for collimating an x-ray beam of a computed tomography scanner after the x-ray beam has passed through a patient being scanned. The collimator includes two elongated parallel plates arranged side by side to define a collimating slit between the plates. At least one of the plates is movably relative to the other plate for varying a width of the collimating slit. The collimator also includes a movable cam operatively arranged with respect to the at least one movable plate such that movement of the cam in a first direction causes the width of the collimating slit to increase, while movement of the cam in a second direction causes the width of the collimating slit to decrease.

42 Claims, 8 Drawing Sheets

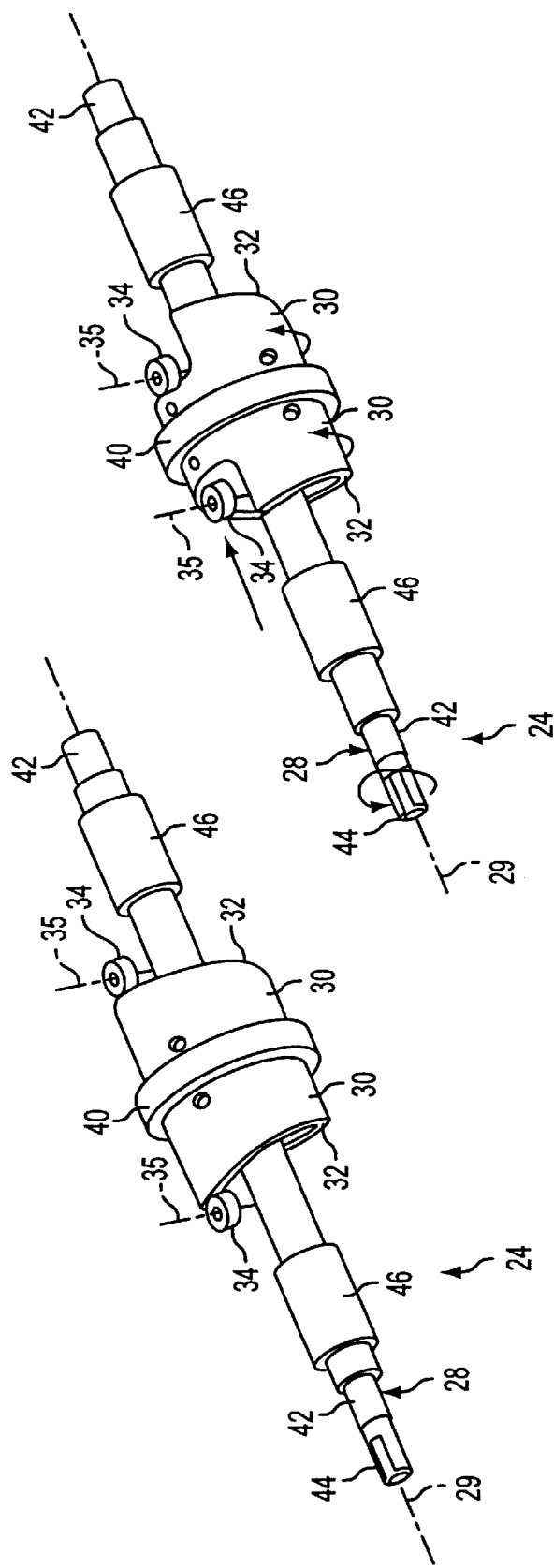

ADJUSTABLE X-RAY COLLIMATOR

This application claims the benefit of U.S. provisional application No. 60/221,944, filed Jul. 31, 2000.

FIELD OF THE DISCLOSURE

The present disclosure relates to the field of radiography and, in particular, relates to computed tomography scanners. Even more particularly, the present disclosure relates to an adjustable x-ray beam collimator for use with a computed tomography scanner.

BACKGROUND OF DISCLOSURE

In computed tomography a patient to be examined is positioned in a scan circle of a computed tomography (CT) scanner. A shaped x-ray beam is then projected from an x-ray source through the scan circle and the patient, to an array of radiation detectors. By rotating the x-ray source and the detector array about the patient (about a z-axis of the scanner), radiation is projected through an imaged slice of the patient to the detectors from a multiplicity of directions. From data provided by the detectors, an image of the scanned slice of the patient is constructed.

Within the x-ray source, an electron beam strikes a focal spot or line on an anode, and x-rays are generated at the focal spot and emitted along diverging linear paths in an x-ray beam. Collimators are normally employed for shaping a cross-section of the x-ray beam, and for directing the shaped beam toward the detector array. A pre-patient collimator is positioned between the x-ray source and the patient, while a post-patient collimator is positioned between the patient and the detector array. Conventional collimators generally comprise a plate-like structure provided with a rectangular slit of uniform width for producing a rectangular beam cross-section, as desired with systems employing a rectangular detector array.

Some CT scanners allow for flexibility in the number and thickness of slices acquired during a scan. In such scanners, the x-ray beam is collimated such that its cross-section irradiates a particular row, or rows of detectors, without irradiating adjacent rows of detectors not utilized for that scan.

What is desired, therefore, is an improved collimator for shaping a cross-section of a beam of energy, and for directing the shaped beam toward a desired target, such as a detector array. What is further desired is an adjustable collimator that produces beam cross-sections of variable widths. Preferably, the collimator will also produce beam cross-sections of variable, yet uniform widths, such that cross-sections will irradiate a specific row, or rows of detectors, without irradiating adjacent rows of detectors.

SUMMARY OF DISCLOSURE

The present disclosure, accordingly, is director to an adjustable collimator for collimating a beam of energy emitted from a focal spot of a beam source. The collimator is particularly intended for collimating an x-ray beam of a computed tomography scanner after the x-ray beam has passed through a patient being scanned.

The collimator generally includes two elongated parallel plates arranged side by side to define a collimating slit between the plates. At least one of the plates is movably relative to the other plate for varying a width of the collimating slit. The collimator also includes a movable cam operatively arranged with respect to the at least one movable plate such that movement of the cam in a first direction causes the width of the collimating slit to increase, while movement of the cam in a second direction causes the width of the collimating slit to decrease.

According to one aspect of the disclosure, the cam is rotatably movable and the collimator includes a motor having has a rotatable shaft coupled to the cam for controlling the width of the collimating slit. According to another aspect, the motor comprises a step motor for providing the collimating slit with predefined, discrete widths. Preferably, the variable slit of the collimator has a uniform width and is curved about a common axis of curvature for alignment with a focal spot of a beam source, such that the collimating slit produces beam cross-sections of variable, yet uniform widths.

The present disclosure also provides a computed tomography scanner including a collimator as described above, and further including an annular gantry rotatable about a rotation axis, a beam source mounted within the gantry and having a focal spot for emitting an x-ray beam through the rotation axis, and an array of x-ray detectors for receiving the x-ray beam from the focal spot. The collimator is mounted within the gantry between the focal spot and the detectors for collimating the x-ray beam. According to one aspect, the collimator is positioned between the axis of rotation and the detector array to act as a "post-patient" collimator.

BRIEF DESCRIPTION OF DRAWINGS

The foregoing and other features and advantages of the present disclosure will become more readily apparent from the following detailed description of the disclosure, as illustrated in the accompanying drawing figures wherein:

FIGS. 7 and 8 are enlarged top isometric views of a cam mechanism according to the present disclosure for use as part of the collimator of FIG. 3, wherein linear movement of cam followers in response to rotary movement of the cams is progressively shown in the two figures.

DETAILED DESCRIPTION OF DISCLOSURE

Figure 1:
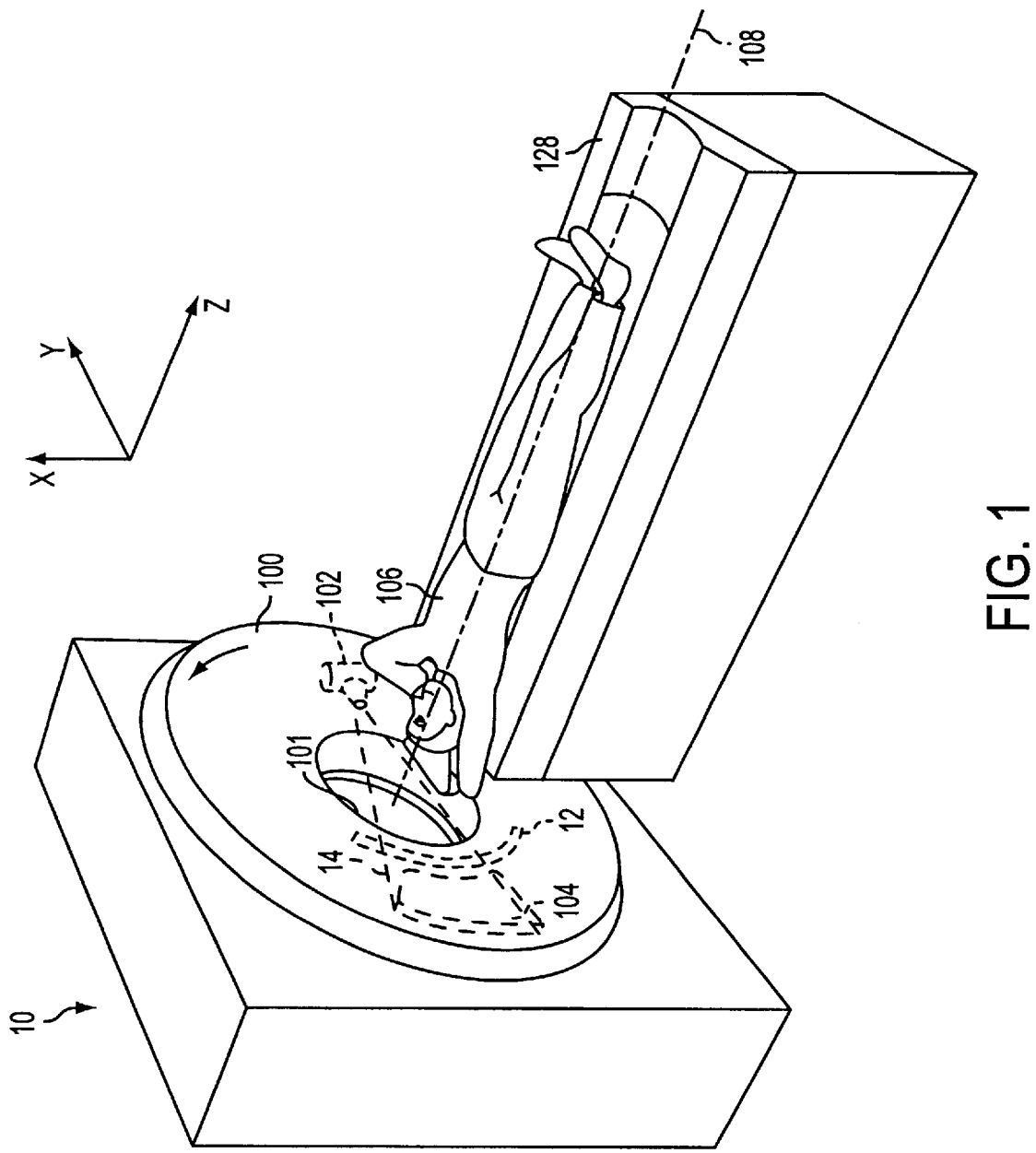
FIG. 1 is a perspective view of a patient positioned on a computed tomography (CT) scanner including a collimator constructed in accordance with the present disclosure.
Figure 2:
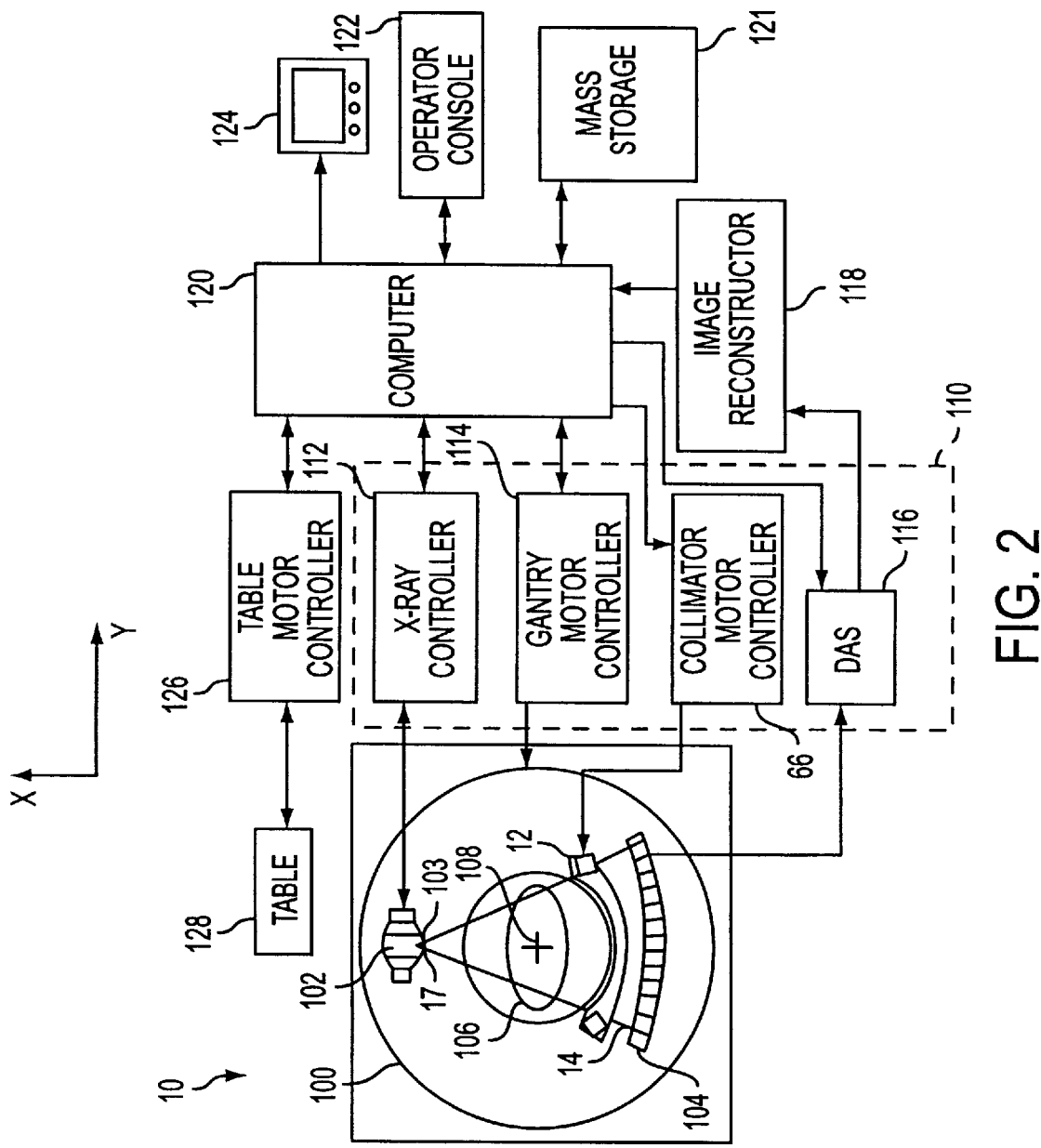
FIG. 2 is a block schematic diagram of the scanner of FIG. 1.

Referring first to FIGS. 1 and 2, a computed tomography (CT) imaging system, or scanner 10 is shown that employs a collimator 12 constructed in accordance with the present disclosure. The collimator 12 is adjustable such that it can provide an x-ray beam 14 produced by the scanner 10 with cross-sections of variable widths, as desired.

In FIGS. 3 through 6, wherein like reference characters refer to the same parts throughout the different views, the collimator 12 is shown in greater detail. Cross-sections of beams are shaped by passing through a slit 16 of the collimator 12. Preferably, the slit 16 is provided in the shape of an elongated, substantially uniform rectangle so that a beam passing through the slit 16 is provided with an elongated, substantially uniform rectangle cross-section. The collimator 12 is made adjustable by providing the slit 16 with an adjustable width w. Variable width x-ray beams are desirable, for example, in CT scanners that allow for flexibility in the number and thickness of slices acquired during a scan. In such a scanner 10, the x-ray beam 14 is collimated such that its cross-section irradiates a particular row, or rows of detectors, without irradiating adjacent rows of detectors not utilized for that scan.

The collimator 12 generally includes two elongated segments 18 that each include an elongated. plate 20. Inner edges 21 of the elongated plates 20 actually form the collimating slit 16. The collimator segments 18 extend between opposing supports 22, which secure the collimator 12 within the CT scanner 10.

Referring also to FIGS. 7 and 8, the presently disclosed collimator 12 is provided with novel, yet simple cam mechanisms 24 for allowing rotary motors 26 to be employed for precisely adjusting the width w of the slit 16 of the collimator 12 by moving the collimator segments 18 on the supports 22. In particular, the cam mechanisms 24 translate the rotational movement of the motors 26 into linear movement of the collimator segments 18 in directions normal to the elongated slit 16, whereby the width w of the slit 16 can be adjusted.

Each cam mechanism 24 includes an elongated rotatable shaft 28 having two identical cams 30 fixed to the shaft for rotation therewith. The cams 30 include cam surfaces 32 facing outwardly in opposing linear directions with respect to axes 29 of the shafts 28. Each cam mechanism 24 also includes cam followers 34, which are secured to the movable collimator segments 18. As shown, the cam followers are preferably provided as rollers 34, which are mounted to the collimator segments 18 such that the rollers 34 are able to rotate about axes 35 generally normal to the axes 29 of the shafts 28. The rollers 34, therefore, reduce friction between the cam surfaces 32 and the movable collimator segments 18 as the cams 30 are rotated.

As shown in FIGS. 7 and 8, as the shafts 28 and the cams 30 are rotated, the cam followers 34 are allowed to move linearly in a direction parallel to the axes 29 of the shafts 28. In particular, the cam surfaces 32 are shaped so that, as the cams 30 are rotated in a counter-clockwise direction, the cam followers 34 of each mechanism 24 are allowed to move inwardly towards the cams 30 in a direction parallel with the axes 29 of the shafts 28. As the cams 30 are rotated in a clockwise direction, the cam followers 34 are pushed outwardly by the cam surfaces 32, away from the cams 30 in a direction parallel with the axes 29 of the shafts 28.

The cam mechanism 24 is shown in an open position in FIG. 7, and shown in a closed position in FIG. 8.

Figure 9:
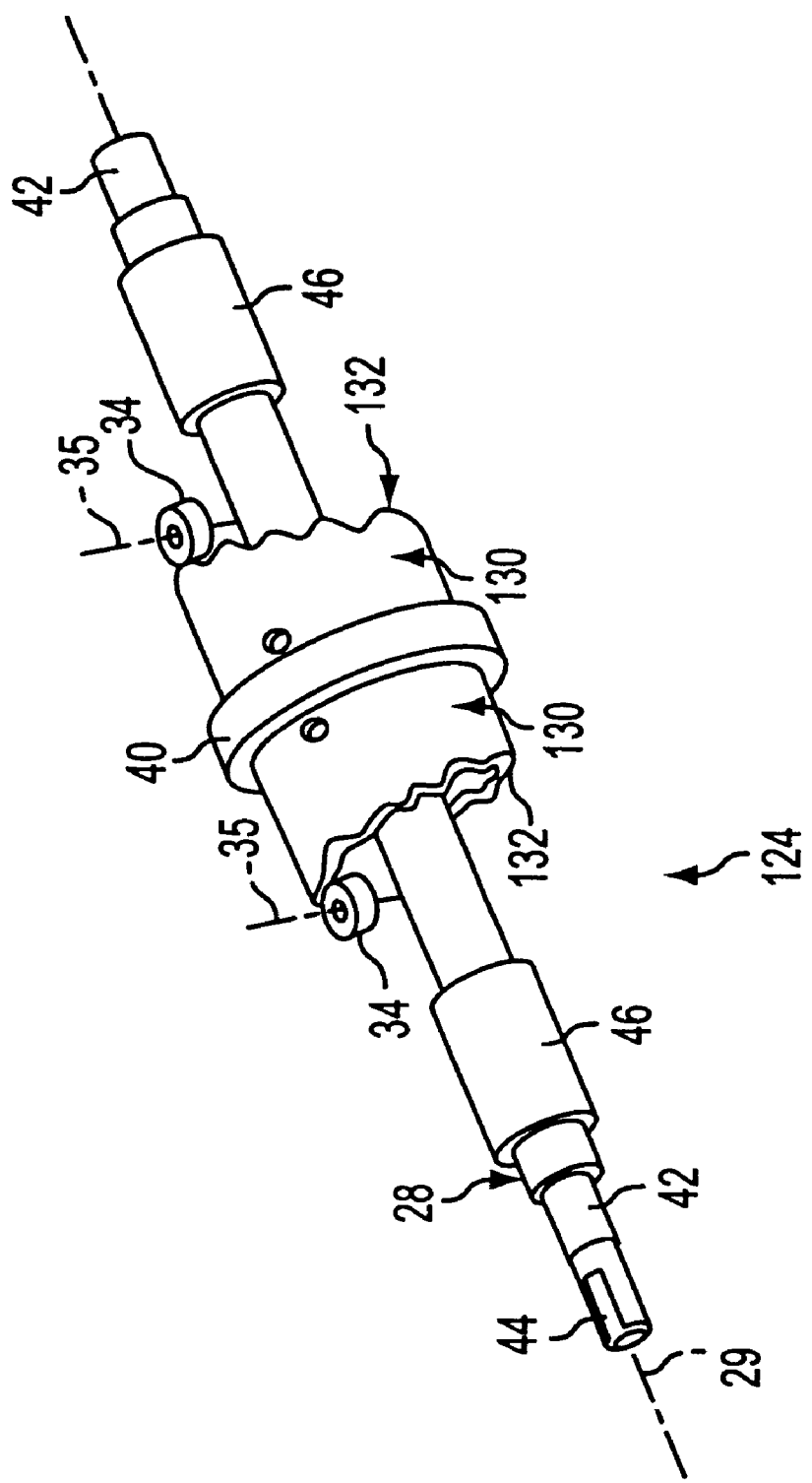
FIG. 9 is a top isometric view of another cam mechanism according to the present disclosure for use as part of the collimator of FIG. 3.

The cam surfaces 32 of the cam mechanism 24 of FIGS. 7 and 8 are generally smooth and thus provide a linear increase or decrease in the width w of the collimating slit 16. Referring to FIG. 9, another cam mechanism 124 according to the present disclosure is shown. The cam mechanism 124 is similar to the cam mechanism 24 of FIGS. 7 and 8, and elements that are the same have the same reference numerals. The cam mechanism 124 of FIG. 9, however, includes cams 130 having cam surfaces 132 with steps formed thereon. The stepped cam surfaces 132 cause the width w of the collimating slit 16 to increase and decrease in discrete steps or increments as the cams 130 are rotated. For example, the steps may be formed in the cam surface 132 such that the width w of the slit 16 increases and decreases in one-millimeter increments.

Referring back to FIGS. 4 through 6, the collimator 12 also includes springs 36 biasing the two segments 18 against the cams 30. The springs 36 can comprise helical metal compression springs or compression bands of resilient rubber or synthetic rubber material, for example. The springs 36 are stretched between corresponding bosses 38 of the collimator segments 18 to pull the segments together, and towards the cams 30. The collimator segments 18 are shown in an open position in FIG. 4 (wherein the slit 16 is at its maximum width w), and shown in a closed position in FIGS. 5 and 6 (wherein the slit 16 is at its minimum width w).

Rotary bearings 40 are received coaxially on recesses 42 in the shafts 28, and each shaft has a shaped end 44 for engagement by the motors 26. The shafts 28 also coaxially receive linear-rotary bearings 46 for supporting the collimator segments 18, such that shafts 28 can rotate with respect to the collimator segments 18 and the collimator segments 18 can linearly slide with respect to the shafts 28. Preferred linear-rotary bearings 46 are available, for example, from Berg Manufacturing of East Rockaway, N.Y. (http://www.wmberg.com).

Referring to FIGS. 3 through 6, each collimator 12 segment includes the collimator plate 20 and a radial frame portion 48 extending normal from an outer edge of the plate. Sleeves 50 extend from opposite ends of the radial frame portions 48 and receive the linear-rotary bearings 46 of the cam mechanisms 24, such that the collimator segments 18 can slide on the shafts 28 of the cam mechanisms 24 to vary the width w of the collimating slit 16.

Figure 4:
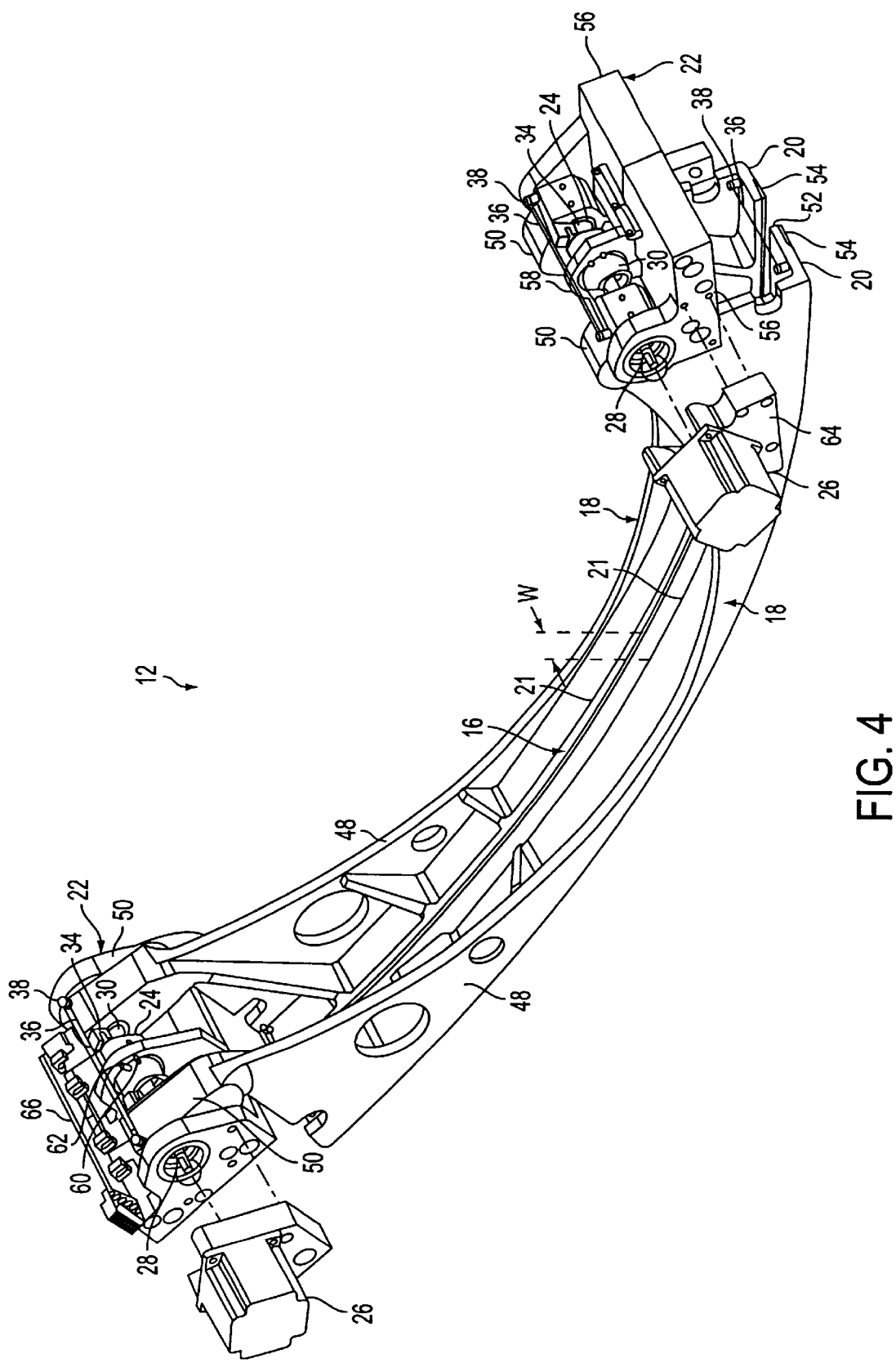
FIG. 4 is a partially exploded, side isometric view of the collimator of FIG. 3.
Figure 5:
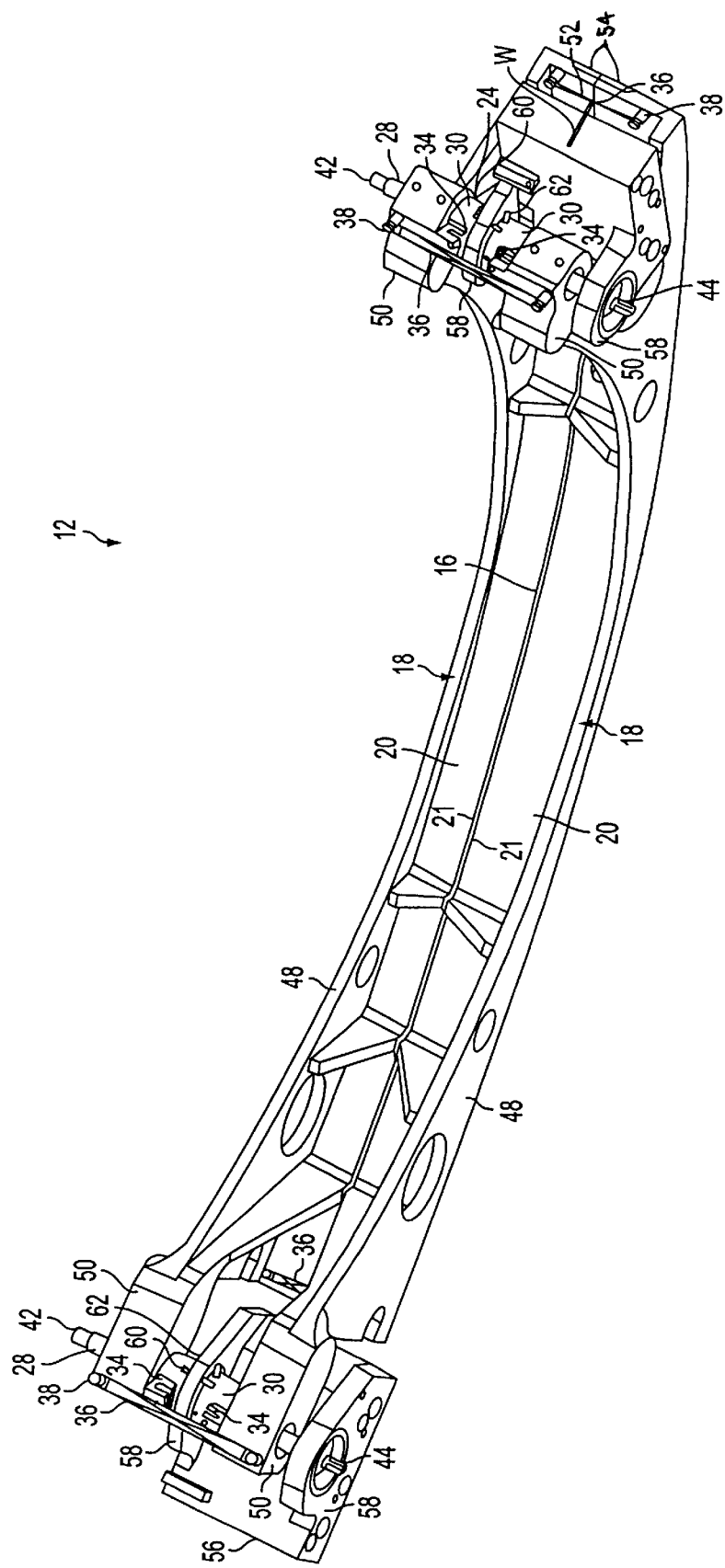
FIG. 5 is a top isometric view of the collimator of FIG. 3.

The collimating slit 16 is formed by the inner edges 21 of the plates 20 of the segments 18. Preferably, one of the edges 21 has protrusions 52, as best shown in FIGS. 4 and 5, so that the slit 16 will have a predefined minimum width w, as shown in FIG. 5. The collimator segments 18 also include lead alloy strips 54 secured to the inner edges 21 of the plates 20 to more precisely define an x-ray profile. The collimator plates 20 are preferably curved about a common axis of curvature, so that all points of the slit 16 are equally spaced from the common axis of curvature.

Figure 6:
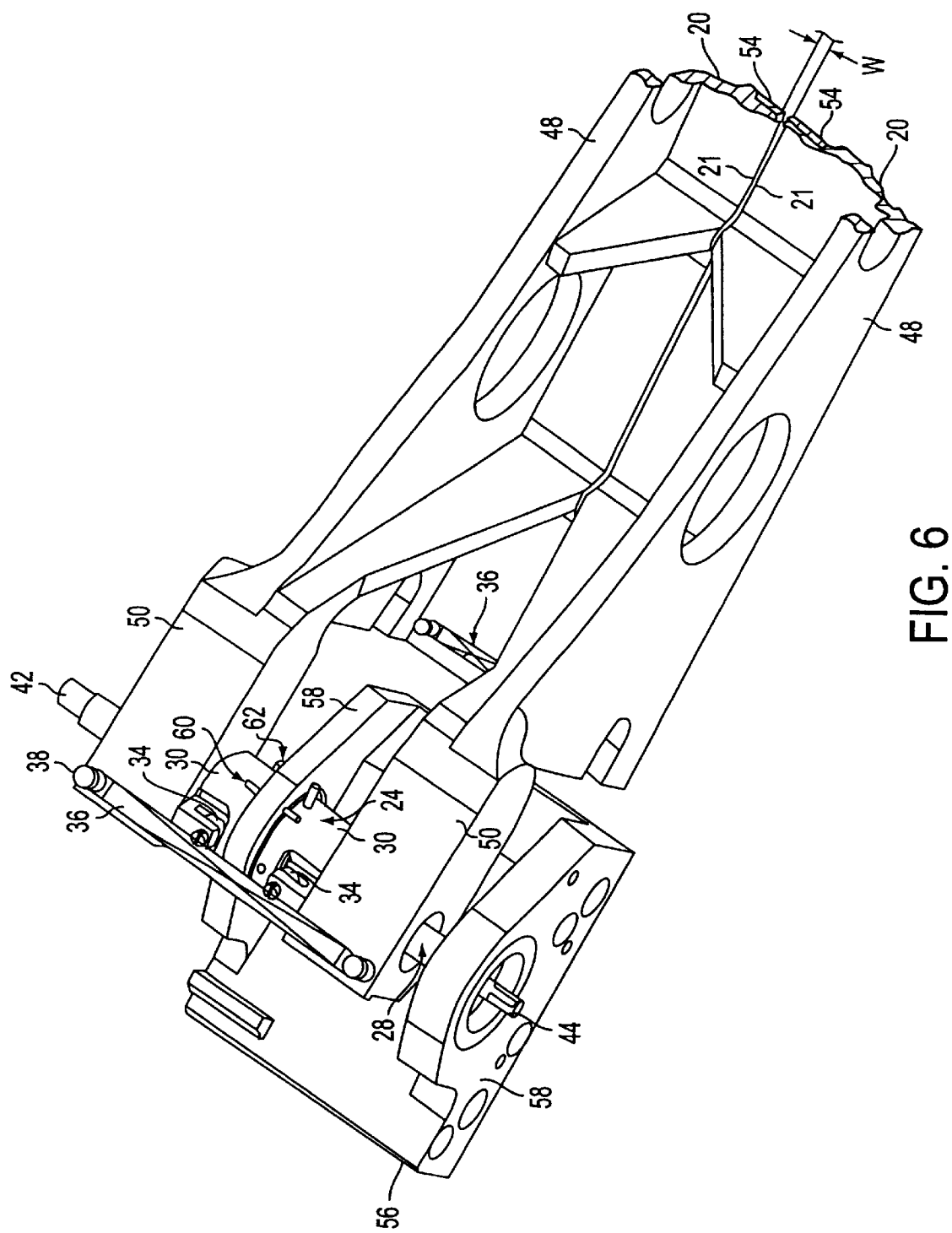
FIG. 6 is an enlarged top isometric view of a portion of the collimator of FIG. 3.

The supports 22 each include mounting blocks 56 having annular retainers 58 receiving the rotary bearings 40 of the cam mechanisms 24 such that the bearings are free to rotate within the retainers. As shown in FIGS. 4 through 6, central retainers 58 of the supports 22 include prongs 60 extending outwardly therefrom, which intercept prongs 62 radially extending from the cams 30 and act as stops to limit the total rotation of the cam mechanisms 24. The motors preferably comprise two synchronized stepping motors 26, which are mounted via mounting plates 64 to the supports 22 such that the motor engages the shaped ends 44 of the shafts 28. The synchronized stepping motors 26 are controlled by a controller 66 having a counter for determining the width w of the slit 16 based upon the stepped rotations of the motors 26. A similar controller and counter combination is shown for example in U.S. Pat. No. 5,550,886 to Dobbs et al. entitled "X-ray Focal Spot Movement Compensation System", which is assigned to the assignee of the present disclosure and which is incorporated herein by reference in its entirety.

Referring back to FIGS. 1 and 2, in addition to the collimator 12, the CT scanner 10 includes an annular gantry 100 having an x-ray source 102 that projects the beam 14 of x-rays toward a detector array 104 on an opposite side of the gantry 100. The x-ray beam 14 is collimated to lie within in an x-y plane of a Cartesian coordinate system and generally referred to as an "imaging plane". The detector array 104 is formed by detector elements, which together sense the projected x-rays 14 that pass through a patient 106. Each detector element 104 produces an electrical signal that represents the intensity of an impinging x-ray beam 14 and hence the attenuation of the beam as it passes through patient 106. During a scan to acquire x-ray projection data, the annular gantry 100 and the components mounted thereon rotate about a center of rotation 108, which is parallel with a z-axis of the Cartesian coordinate system.

As shown in FIG. 2, rotation of the gantry 100 and the operation of the x-ray source 102 are governed by a control mechanism 110 of the CT scanner 10. The control mechanism 110 includes an x-ray controller 112 that provides power and timing signals to the x-ray source 102 and a gantry motor controller 114 that controls the rotational speed and position of the gantry 100. A data acquisition system (DAS) 116 of the control mechanism 110 samples analog data from the detector elements 104 and converts the data to digital signals for subsequent processing. An image reconstructor 118 receives sampled and digitized x-ray data from the DAS 116 and performs high speed image reconstruction, which is applied as an input to a computer 120 which stores the image in a mass storage device 121.

The computer 120 receives commands and scanning parameters from an operator via an input device, such as a keyboard 122, and a video display 124 allows the operator to observe the reconstructed image and other data from computer. The operator supplied commands and parameters are used by the computer 120 to provide control signals and information to the DAS 116, the x-ray controller 112 and the gantry motor controller 114. In addition, the computer controls a table motor controller 126 which controls a motorized table 128 to position the patient 106 through a central opening 101 in the gantry 100. In particular, the table moves portions of the patient 106 through the annular gantry 100 in a direction parallel with the rotation axis 108 of the gantry.

Figure 3:
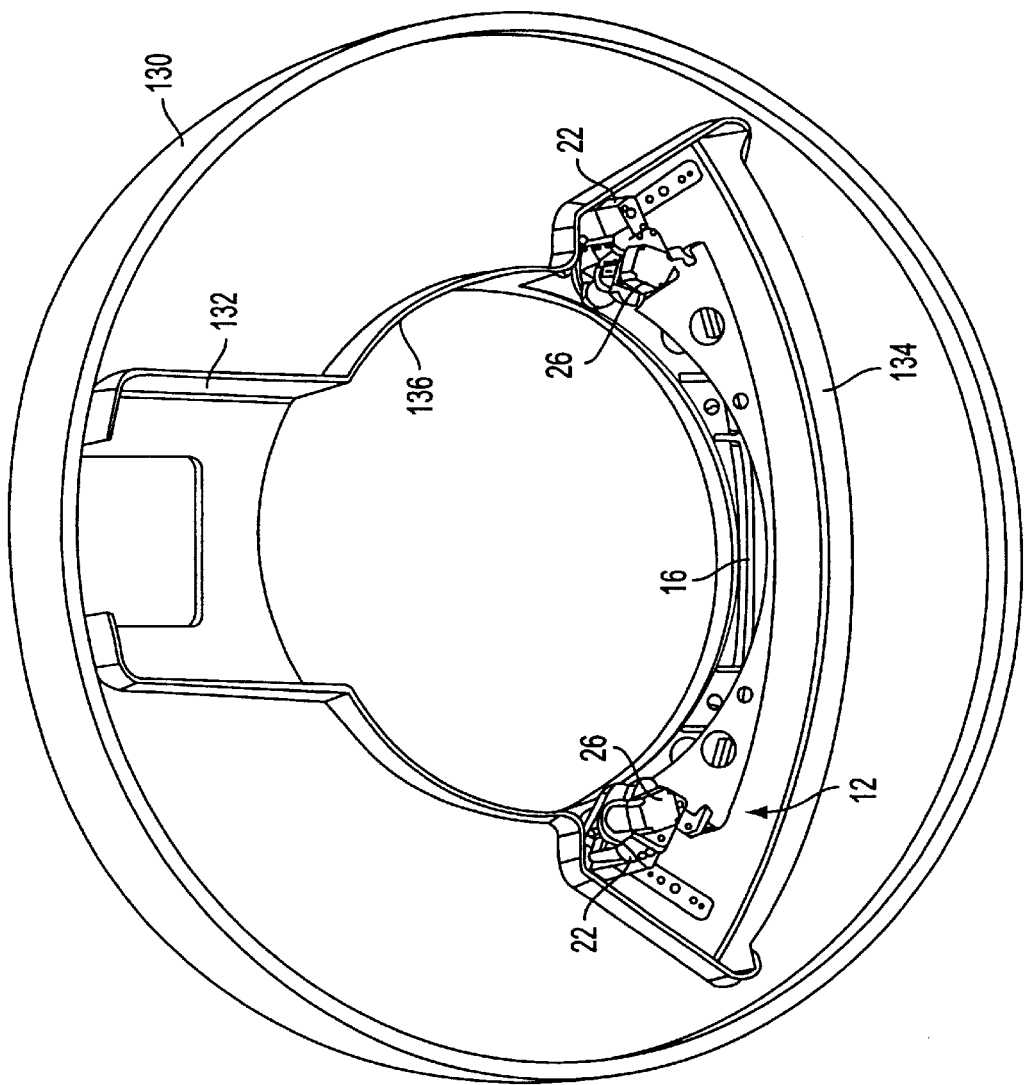
FIG. 3 is an end isometric view of the collimator of the present disclosure mounted on a gantry frame of the scanner of FIG. 1.

The collimator 12 of FIGS. 3 through 8, is mounted within a frame 130 of the annular gantry 100 of the scanner 10, as shown in FIG. 3. In particular, the supports 22 of the collimator 12 are secured to the gantry frame 130 with suitable fasteners, such as steel bolts. The gantry frame 130 also includes receptacles 132, 134 for receiving, respectively, the x-ray beam source 102 and the detector array 104 on either side of the collimator 12. As shown in FIG. 3, the collimator 12 is mounted between an opening 136 of the annular frame 130 and the receptacle 134 for the detector array 104. Referring also to FIGS. 1 and 2, the collimator 12 is positioned in the gantry 100 between the opening 101 of the annular gantry 100 and the array of detectors 104. In this position, the collimator 12 collimates the x-ray beam 14 of the CT scanner 10. after the x-ray beam has passed through a patient 106 being scanned within the opening 101 of the annular gantry 100. The collimator 12 is utilized as a "post-patient" collimator, and is suitably sized for that role.

As shown in FIG. 2, the collimator 12 is also mounted in the gantry 100 so that the axis of curvature 17 of the collimator 12 intersects a focal spot 103 of the x-ray source of the scanner 10, whereby all points of the collimating slit 16 are equally spaced from the focal spot. In this manner, the slit 16 of the collimator 12 produces a shaped x-ray beam having a cross-section that is of substantially uniform width throughout. The collimator motor controller 66 is preferably connected to the computer 120 of the CT scanner 10.

While an adjustable collimator 12 constructed in accordance with the present disclosure has been particularly shown and described with reference to the embodiment of FIGS. 3–8, it should be understood that the particular embodiment is intended by way of illustration and example only and is not to be taken by way of limitation. Various changes can be made to the particular embodiment described without departing from the spirit and scope of an adjustable collimator 12 as defined by the appended claims. For example, while the presently disclosed collimator 12 has been shown and described with particular reference to x-ray beams of CT scanners, it is to be appreciated that the disclosure may find further application in other areas of radiography, such as medical diagnostic digital x-ray, conventional x-ray, radiation therapy, and the like.

In addition, the collimator 12 is shown being utilized as a "post-patient" collimator, i.e., the collimator 12 collimates the x-ray beam of the CT scanner after the x-ray beam has. passed through a patient being scanned. The unique features of the presently disclosed collimator 12, however, are not meant to be limited for use with a post-patient collimator, and can be applied to any type of collimator where adjustable beam widths are desired.

Furthermore, the cam followers 34 of the collimator 12 can be provided as a unitary piece of the collimator segments 18, instead of as separate rotatable rollers. It is also envisioned that linearly movable cams can be used to move the collimator segments 18 in place of the rotary movable cams 30. In addition, the collimator 12 can be arranged such that the springs 36 bias the collimating slit 16 in an open position instead of a closed position, and the cams 30 can be positioned outside of the segments 18 instead of between the segments. Accordingly, the spirit and scope of the present disclosure are to be limited only by the terms of the appended claims.

What is claimed is:

1. A collimator for shaping a beam of energy emitted from a focal spot of a beam source, the collimator comprising:

two elongated parallel plates arranged side by side to define an elongated collimating slit between the plates, wherein at least one of the plates is movably relative to the other plate for varying a width of the collimating slit; and a movable cam operatively arranged with respect to the at least one movable plate such that movement of the cam in a first direction causes the width of the collimating slit to increase, and movement of the cam in a second direction causes the width of the collimating slit to decrease, wherein the at least one movable plate includes a follower contacting a cam surface of the cam, and wherein the cam surface includes steps.

2. A collimator according to claim 1, wherein the cam is rotatably movable.

3. A collimator according to claim 2, further including a motor having a rotatable shaft coupled to the cam.

4. A collimator according to claim 1, further including a motor for moving the cam.

5. A collimator according to claim 4, wherein the motor comprises a stepping motor, and the collimator also includes a motor controller having a counter for counting steps of the steping motor and a memory for saving the count.

6. A computed tomography scanner including a collimator according to claim 1, and further including:

an annular gantry rotatable about a rotation axis;

a beam source mounted within the gantry and having a focal spot for emitting an x-ray beam through the rotation axis; and an array of x-ray detectors for receiving the x-ray beam from the focal spot;

wherein the collimator is mounted within the gantry between the focal spot and the detectors for collimating the x-ray beam.

7. A scanner according to claim 6, wherein the collimator is located between the rotation axis of the gantry and the detectors.

8. A scanner according to claim 7, wherein the plates of the collimator each have curved side profiles sharing a common axis of curvature intersecting the focal spot of the beam source.

9. A collimator according to claim 1, wherein both plates are movable.

10. A collimator according to claim 1, further including at least one spring biasing the movable plate towards the cam.

11. A collimator according to claim 10, wherein the spring biases the plates together and the cam is positioned between the plates.

12. A collimator according to claim 10, wherein the spring comprises a compression band of resilient material stretched between the plates.

13. A collimator according to claim 1, wherein the plates each have curved side profiles sharing a common axis of curvature.

14. A collimator according to claim 1, wherein the collimating slit has a predetermined minimum width.

15. A collimator for shaping a beam of energy emitted from a focal spot of a beam source, the collimator comprising:
- two elongated parallel plates arranged side by side to define an elongated collimating slit between the plates, wherein at least one of the plates is movably relative to the other plate for varying a width of the collimating slit; and
- a movable cam operatively arranged with respect to the at least one movable plate such that movement of the cam in a first direction causes the width of the collimating slit to increase, and movement of the cam in a second direction causes the width of the collimating slit to decrease, wherein the at least one movable plate includes a follower contacting a cam surface of the cam, and wherein the follower is rotatable.

16. A collimator according to claim 15, wherein the cam surface is substantially smooth.

17. A collimator according to claim 15, wherein both plates are movable.

18. A computed tomography scanner including a collimator according to claim 15, and further including:
- an annular gantry rotatable about a rotation axis;
- a beam source mounted within the gantry and having a focal spot for emitting an x-ray beam through the rotation axis; and
- an array of x-ray detectors for receiving the x-ray beam from the focal spot;
- wherein the collimator is mounted within the gantry between the focal spot and the detectors for collimating the x-ray beam.

19. A scanner according to claim 18, wherein the collimator is located between the rotation axis of the gantry and the detectors.

20. A scanner according to claim 19, wherein the plates of the collimator each have curved side profiles sharing a common axis of curvature intersecting the focal spot of the beam source.

21. A collimator according to claim 15, wherein the cam is rotatably movable.

22. A collimator according to claim 21, further including a motor having a rotatable shaft coupled to the cam.

23. A collimator according to claim 15, further including a motor for moving the cam.

24. A collimator according to claim 23, wherein the motor comprises a stepping motor, and the collimator also includes a motor controller having a counter for counting steps of the stepping motor and a memory for saving the count.

25. A collimator according to claim 15, further including at least one spring biasing the movable plate towards the cam. together and the cam is positioned between the plates.

26. A collimator according to claim 25, wherein the spring biases the plates together and the cam is positioned between the plates.

27. A collimator according to claim 25, wherein the spring comprises a compression band of resilient material stretched between the plates.

28. A collimator according to claim 15, wherein the plates each have curved side profiles sharing a common axis of curvature.

29. A collimator according to claim 15, wherein the collimating slit has a predetermined minimum width.

30. A collimator for shaping a beam of energy emitted from a focal spot of a beam source, the collimator comprising:
- two elongated parallel plates arranged side by side to define an elongated collimating slit between the plates, wherein at least one of the plates is movably relative to the other plate for varying a width of the collimating slit;
- a movable cam operatively arranged with respect to the at least one movable plate such that movement of the cam in a first direction causes the width of the collimating slit to increase, and movement of the cam in a second direction causes the width of the collimating slit to decrease;
- a rotatable shaft extending generally normal to the collimating slit, wherein the cam is mounted on the shaft for rotation therewith and the at least one movable plate is slidingly received on the shaft; and
- a follower extends from the movable plate and contacts a cam surface of the cam;
- whereby rotation of the shaft and the cam causes the movable plate to slide on the shaft.

31. A computed tomography scanner including a collimator according to claim 14, and further including:
- an annular gantry rotatable about a rotation axis;
- a beam source mounted within the gantry and having a focal spot for emitting an x-ray beam through the rotation axis; and
- an array of x-ray detectors for receiving the x-ray beam from the focal spot;
- wherein the collimator is mounted within the gantry between the focal spot and the detectors for collimating the x-ray beam.

32. A scanner according to claim 31, wherein the collimator is located between the rotation axis of the gantry and the detectors.

33. A scanner according to claim 32, wherein the plates of the collimator each have curved side profiles sharing a common axis of curvature intersecting the focal spot of the beam source.

34. A collimator according to claim 30, further including a motor for rotating the shaft.

35. A collimator according to claim 34, wherein the motor comprises a stepping motor, and the collimator also includes a motor controller having a counter for counting steps of the stepping motor and a memory for saving the count.

36. A collimator according to claim 30, further including at least one spring biasing the movable plate towards the cam.

37. A collimator according to claim 36, wherein the spring biases the plates together and the cam is positioned between the plates.

38. A collimator according to claim 36, wherein the spring comprises a compression band of resilient material stretched between the plates.

39. A collimator according to claim 30, wherein the plates each have curved side profiles sharing a common axis of curvature.

40. A collimator according to claim 30, wherein the collimating slit has a predetermined minimum width.

41. A collimator according to claim 30, wherein both plates are movable.

42. A collimator according to claim 30, further comprising a linear-rotary bearing supporting the plate on the shaft.

* * * * *

UNITED STATES PATENT AND TRADEMARK OFFICE
CERTIFICATE OF CORRECTION

PATENT NO.   : 6,449,340 B1                                                      Page 1 of 1
DATED        : September 10, 2002
INVENTOR(S)  : Andrew P. Tybinkowski et al.

It is certified that error appears in the above-identified patent and that said Letters Patent is hereby corrected as shown below:

<u>Column 7,</u>
Line 59, after "cam.", delete " together and the cam is positioned between the plates. ";

<u>Column 8,</u>
Line 26, after "claim", delete "14" and insert therefor -- 30 --.

Signed and Sealed this

Sixth Day of May, 2003

JAMES E. ROGAN
*Director of the United States Patent and Trademark Office*